US011737801B2

(12) United States Patent
Cushen et al.

(10) Patent No.: US 11,737,801 B2
(45) Date of Patent: Aug. 29, 2023

(54) SKULL BASE CLOSURE SYSTEMS AND METHODS

(71) Applicant: Stryker European Holdings I, LLC, Kalamazoo, MI (US)

(72) Inventors: Patrick Eoin Cushen, Cork (IE); Johannes Jacobus Jacobs, Cork (IE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 237 days.

(21) Appl. No.: 17/416,081

(22) PCT Filed: Dec. 20, 2019

(86) PCT No.: PCT/US2019/067835
§ 371 (c)(1),
(2) Date: Jun. 18, 2021

(87) PCT Pub. No.: WO2020/132433
PCT Pub. Date: Jun. 25, 2020

(65) Prior Publication Data
US 2022/0039851 A1 Feb. 10, 2022

Related U.S. Application Data

(60) Provisional application No. 62/782,718, filed on Dec. 20, 2018.

(51) Int. Cl.
*A61B 17/88* (2006.01)
*A61F 2/28* (2006.01)
(Continued)

(52) U.S. Cl.
CPC .......... *A61B 17/88* (2013.01); *A61B 17/8872* (2013.01); *A61B 2017/00628* (2013.01);
(Continued)

(58) Field of Classification Search
CPC ........ A61B 2017/00628; A61B 17/686; A61B 17/688; A61B 17/88; A61B 17/8872;
(Continued)

(56) References Cited

U.S. PATENT DOCUMENTS 6,355,699 B1   3/2002  Vyakarnam et al.
8,740,929 B2   6/2014  Gopferich et al.
(Continued)

FOREIGN PATENT DOCUMENTS

WO    9964491 A1    12/1999
WO    2014035245 A1  3/2014
WO    2020212848 A1 10/2020

OTHER PUBLICATIONS

International Search Report for Application No. PCT/US2019/067835 dated Mar. 26, 2020, 4 pages.

*Primary Examiner* — Larry E Waggle, Jr.
(74) *Attorney, Agent, or Firm* — Howard & Howard Attorneys PLLC

(57) ABSTRACT

The present disclosure provides a bioresorbable foam closure device for trans-nasally closing an opening in a base of a skull. The closure device comprises a phase-separated polymer having a porosity of greater than 80%. The device includes a stem portion having a proximal end and a distal end, and a head portion at the distal end of the stem portion. The closure device is deformed from a free shape to a constricted shape, inserted through a nasal cavity and into the opening, and released to at least partially revert back to the free shape such that the stem portion fills the opening and the head portion abuts cranium and dura to secure the closure device in position and seal the opening.

20 Claims, 7 Drawing Sheets

(51) Int. Cl.
  *A61B 17/00* (2006.01)
  *A61B 50/00* (2016.01)
(52) U.S. Cl.
  CPC .............. *A61B 2050/0072* (2016.02); *A61F 2002/2885* (2013.01)
(58) Field of Classification Search
  CPC ....... A61B 2050/0072; A61B 2090/103; A61F 2002/2835; A61F 2002/2839; A61F 2/2875; A61F 2002/2885
  See application file for complete search history.

(56) References Cited

U.S. PATENT DOCUMENTS

| | | |
|---|---|---|
| 9,084,876 B2 | 7/2015 | Makower et al. |
| 9,101,341 B2 * | 8/2015 | Fitzgerald .......... A61B 17/0057 |
| 2005/0283187 A1 | 12/2005 | Longson |
| 2008/0294255 A1 * | 11/2008 | Gonzales .................. A61F 2/04 |
| | | 623/10 |
| 2009/0171388 A1 | 7/2009 | Dave et al. |
| 2014/0114348 A1 | 4/2014 | Stanley et al. |
| 2018/0028725 A1 | 2/2018 | Tooren et al. |

* cited by examiner

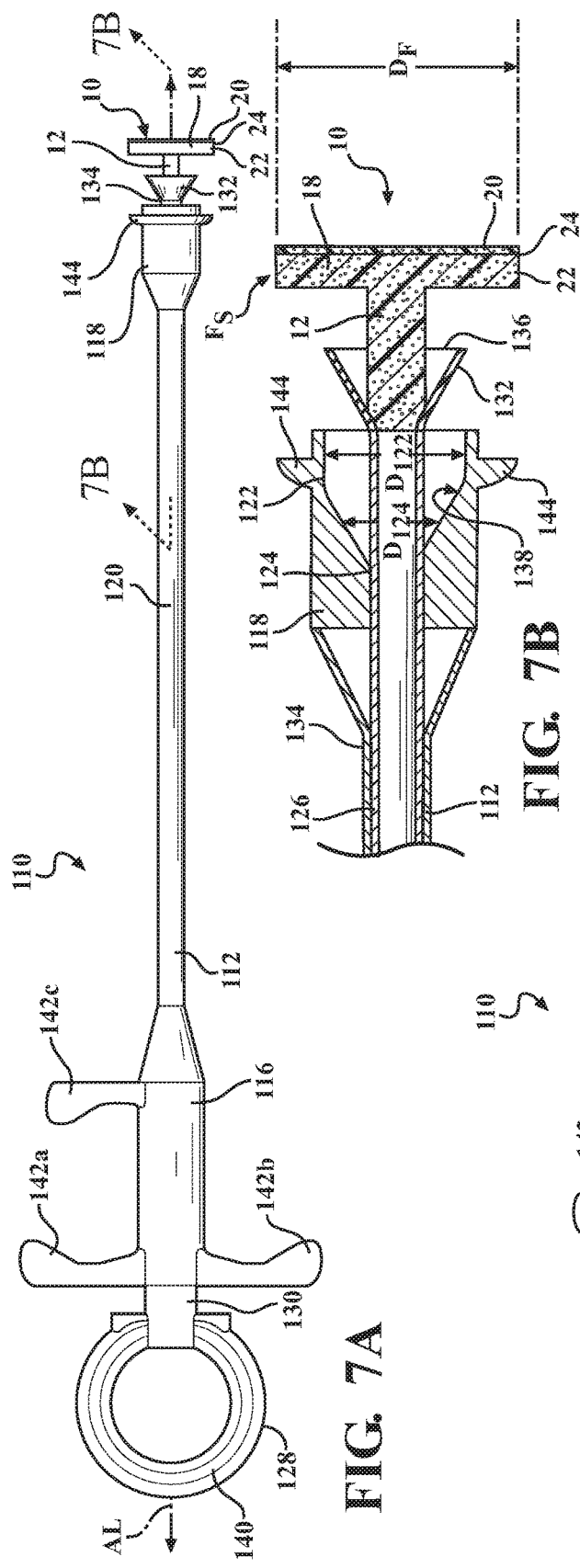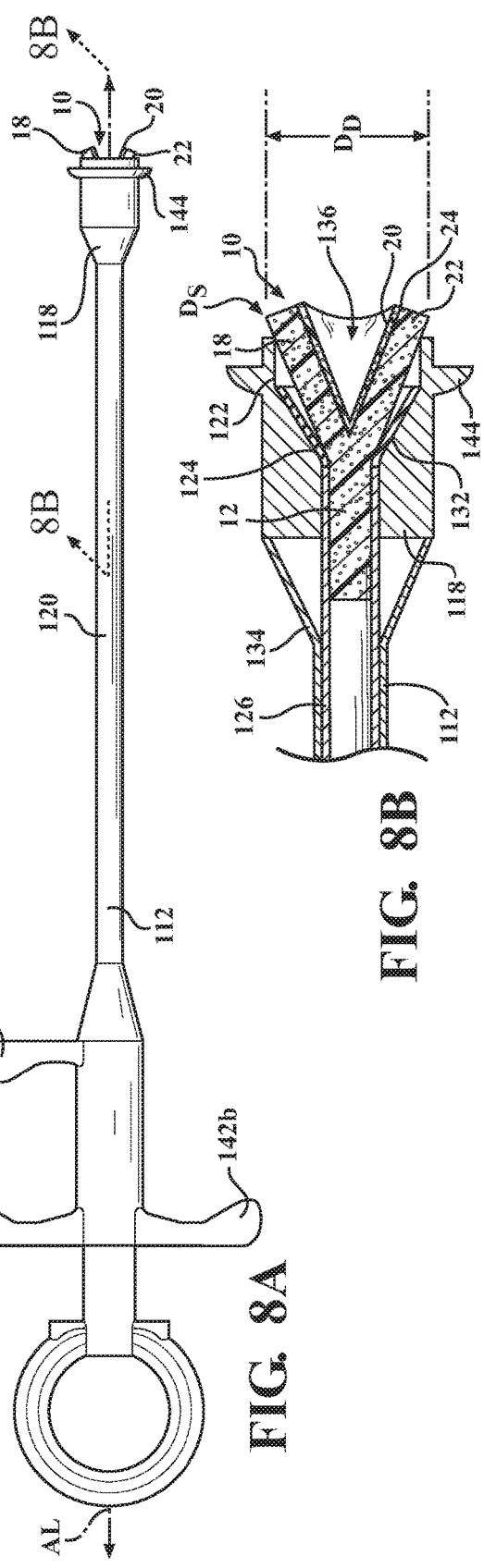

SKULL BASE CLOSURE SYSTEMS AND METHODS

CROSS-REFERENCE TO RELATED APPLICATIONS

The subject application is the National Stage of International Application No. PCT/US2019/067835, filed on Dec. 20, 2019, which claims priority to and all of the benefits of U.S. Provisional Patent Application No. 62/782,718, filed on Dec. 20, 2018, the disclosures of which are hereby incorporated by reference.

BACKGROUND

Trans-nasal skull based surgical techniques have advanced significantly over the years. Repairing large skull base openings and cerebrovascular structures resulting from trans-nasal skull based surgical techniques, e.g. endoscopic trans-nasal craniotomies, remains a difficult challenge. Problems with closure of the skull defect which typically includes a compromised dura mater and prevention of cerebrospinal fluid leaks are a persistent source of complications in both endoscopic and open skull based surgeries. As such, there remains a need for improved materials and methods, which may be used to prevent post-surgical cerebrospinal fluid leaks and promote the repair of large skull base openings and cerebrovascular structures resulting from skull based surgeries.

SUMMARY

The present disclosure provides a bioresorbable foam closure device for trans-nasally closing an opening in a base of a skull. The closure device includes a phase-separated polymer having a porosity of greater than 50%. The device includes a stem portion having a proximal end and a distal end, and a head portion at the distal end of the stem portion.

The present disclosure also provides a surgical tool for placing the closure device in an opening in a base of a skull. The surgical tool includes a body defining an inner channel. The body has a handle, a dispensing tip, and a central section therebetween. The dispensing tip has a tapered profile between a first region and a second region, with the first region having a greater diameter than the second region. A shaft is moveably disposed in the inner channel of the body, the shaft has a control surface at a proximal region and a deformable head at a distal region, the shaft and the deformable head cooperate to define a lumen to accommodate a portion of the closure device. Upon actuation of the control surface, the deformable head moves between a first state in which the deformable head is outside of the second region of the dispensing tip and a second state where the deformable head is at least partially within the second region of the dispensing tip. A diameter of the deformable head in the first state is greater than a diameter of the deformable head in the second state.

A method of trans-nasally closing an opening in a base of a cranium with the closure device and the surgical tool is further disclosed. The method includes the steps of providing the closure device. At least the head portion of the closure device is deformed from a free shape to a deformed shape. Once deformed, the head portion is inserted through a nasal cavity and through the opening such that the head portion is in the cranial cavity and the stem portion extends through the opening and into the nasal cavity. Once released, the closure device at least partially reverts to the free shape such that the stem portion fills the opening and the head portion abuts an inner surface of the cranium as well as dura, thereby securing the closure device in position and sealing the opening.

As such, the subject disclosure provides improved materials and methods, which may be used to prevent post-surgical cerebrospinal fluid leaks and promote the repair of large skull base openings, and cerebrovascular structures resulting from skull based surgeries.

BRIEF DESCRIPTION OF THE DRAWINGS

Advantages of the present disclosure will be readily appreciated as the same becomes better understood by reference to the following detailed description when considered in connection with the accompanying drawings wherein:

FIG. 7A is a perspective view of the closure device and the surgical tool prior to loading the closure device in the surgical tool;

FIG. 7B is cross-sectional view along 7B-7B of the closure device and a distal end of the surgical tool prior to loading;

FIG. 8A is a perspective view of the closure device loaded into a distal end of the surgical tool;

FIG. 8B is cross-sectional view along 8B-8B of the closure device loaded into the distal end of the surgical tool;

Figure 1:
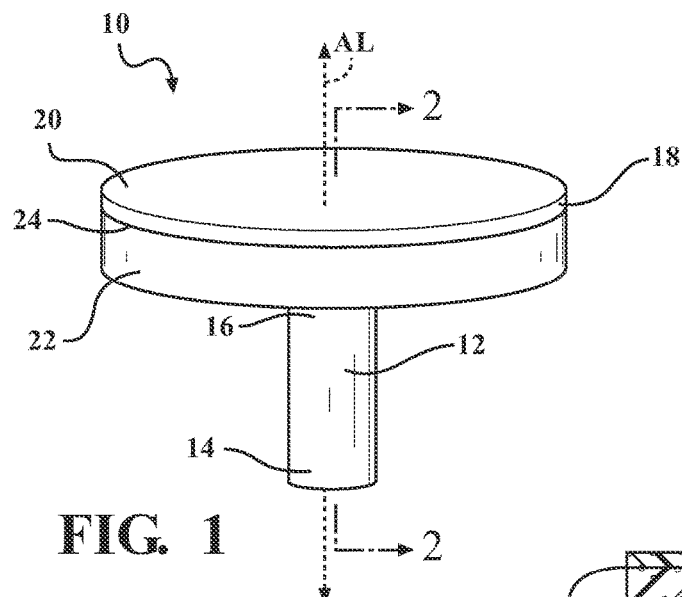
FIG. 1 is a perspective view of an exemplary bioresorbable foam closure device for trans-nasally closing an opening in a base of a skull.
Figure 2:
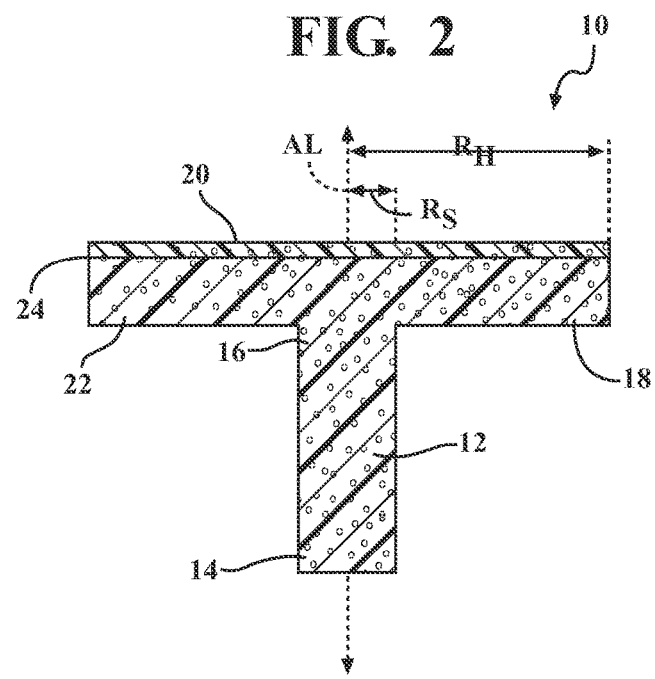
FIG. 2 is a cross-sectional view along 2-2 of the closure device of FIG. 1.
Figure 3:
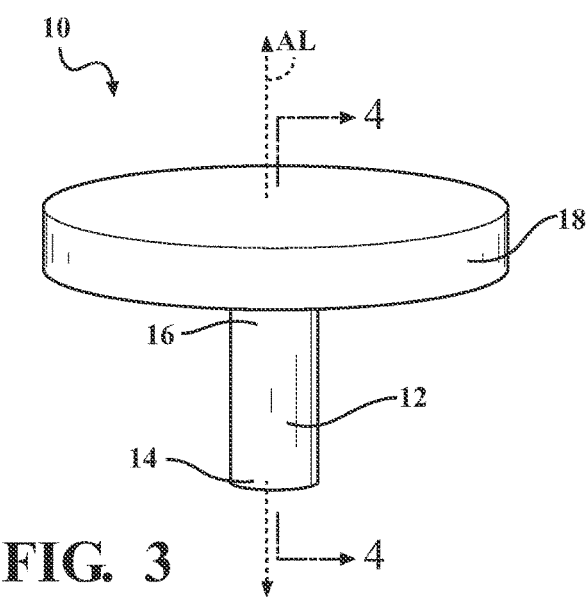
FIG. 3 is a perspective view of another exemplary bioresorbable foam closure device for trans-nasally closing an opening in a base of a skull.
Figure 4:
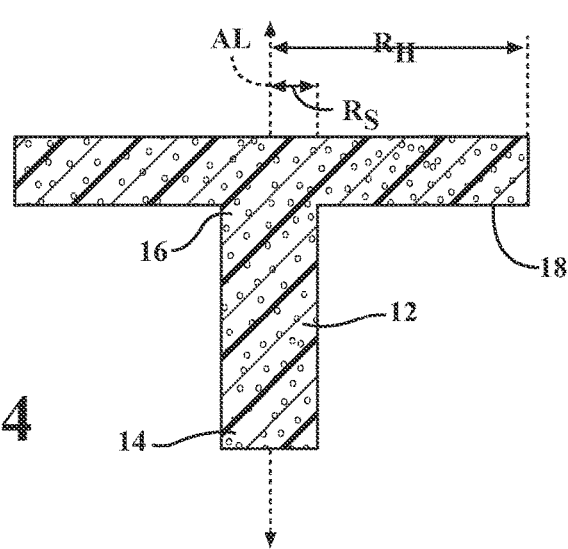
FIG. 4 is a cross-sectional view along 4-4 of the closure device of FIG. 3.

It is to be understood that the drawings are purely illustrative and are not necessarily drawn to scale.

DETAILED DESCRIPTION

Examples of a bioresorbable foam closure device ("closure device") 10 for trans-nasally closing an opening 300 in a base of a skull 302 are shown in FIGS. 1-4. The closure device 10 includes a stem portion 12 having a proximal end 14 and a distal end 16. The closure device 10 also includes a head portion 18 adjacent the distal end 16 of the stem portion 12.

As is explained herein, during use, the closure device 10 is deformed from a free shape to a constricted shape, inserted through a nasal cavity 298 and into the opening 300, and released to at least partially revert back to the free shape such that the stem portion 12 fills the opening 300 and the head portion 18 abuts an inner surface 304 of the skull/cranium 302 as well as dura 308, thereby securing the closure device 10 in position to close and seal the opening 300. Use of the closure device 10 is described in detail below and illustrated in FIGS. 10-13.

Referring now to FIG. 1, the distal end 16 of the stem portion 12 having the head portion 18 thereon is furthest from the surgeon, while the proximal end 14 of the stem portion 12 is closest to the surgeon. In other words, when the closure device 10 is inserted into the nasal cavity 298, the head portion 18 and the distal end 16 of the stem portion 12 are the first end to enter the nasal cavity 298 and the proximal end 14 of the stem portion 12 is relatively close to the surgeon.

The head portion 18 typically has at least one dimension, e.g. a radius, which is larger than a dimension of the stem portion 12. Referring again to FIG. 1, the head portion 18 and the stem portion 12 may share a longitudinal axis $A_L$. In certain shapes, the radius $R_H$ of the head portion 18 relative to the longitudinal axis $A_L$ is greater than the radius $R_S$ of the stem portion 12 relative to the longitudinal axis $A_L$. In the example shown in FIGS. 1 and 2, the stem portion 12 the head portion 18 have a cylindrical shape. More specifically, in the example of FIG. 1, the stem portion 12 is cylindrical and the head portion is concentrically disposed on the distal end 16 of the stem portion 12 and disc shaped (cylindrical). The geometric configuration of the stem portion 12 is not particularly limited. Although the stem portion 12 throughout the Figures is illustrated as cylindrical with a circular cross-sectional profile, it should be appreciated that the stem portion 12 and the head portion could have various cross-sectional profiles including but not limited to ovular (including circular), rectangular (including square), and triangular.

In some examples, the stem portion 12 may include a core portion and a shell portion (not illustrated in the Figures). In one example, the core portion and the shell portion are foamed. The shell portion is arranged such that the foamed core portion is at least partially disposed within the foamed shell portion. Within the context of this disclosure "at least partially disposed within" requires that some volume of the core portion is disposed within a cavity of the shell portion. In certain examples, from 10 to 100%, from 20 to 100%, from 30 to 100%, from 40 to 100%, from 50 to 100%, from 60 to 100%, from 70 to 100%, from 80 to 100%, or from 90 to 100%, of the total volume of the core portion is disposed within the shell portion. In one such example, the shell portion and core portion are adjacent laminar layers.

The closure device 10 of some examples may be shaped with the stem portion 12 of excess length and the head portion 18 of excess area. Such examples allow a user, e.g. a doctor, to tailor the shape of the closure device 10 to a particular nasal cavity 298 and a particular opening 300 by simply cutting the closure device 10 to a desired shape based on the particular opening 300 to be sealed. Of course, the materials from which the closure device 10 of such examples are formed are selected such that they may be cut to the desired shape with surgical scissors, a surgical knife, etc.

As is alluded to above, the closure device 10 is deformable and shaped to close and seal the opening 300 in the skull 302, with the stem portion 12 filling the opening 300 and the head portion 18 abutting the inner surface 304 of the skull/cranium 302. To this end, the head portion 18 may be foldable or collapsible along the longitudinal axis $A_L$ in the distal direction. Alternatively, the head portion may be foldable along a different line/plane. Alternatively, the head portion may be deformable in a manner other than folding. FIG. 7 illustrates the head portion 18 in a free state whereas FIG. 8 illustrates the head portion 18 in a constricted state.

The head portion 18 has a greater perimeter and/or diameter than the stem portion 12. In the example of FIG. 1, the head portion 18 is disc shaped and has both a greater perimeter and diameter than the stem portion 12. The geometric configuration of the head portion 18 is not particularly limited. Although the head portion 18 is illustrated throughout the Figures as having a round cross-sectional profile, it should be appreciated that the head portion 18 could have various cross-sectional profiles including but not limited to ovular (including circular), rectangular (including square), and triangular.

In the example of FIG. 1, the head portion 18 includes a film layer 20 comprising polymer and a foam base 22 comprising the phase-separated polymer. The film layer 20 and the foam base 22 form a bond interface 24 therebetween. The film layer 20 is disposed at the distal end 16 of the closure device 10 and the foam base 22 is disposed between the film layer 20 and the distal end 16 of the stem portion 12 of the closure device 10. When arranged in this manner, the film layer 20 acts as an impermeable or semi-permeable membrane to stop the leakage of cerebrospinal fluid and promote the repair of the opening 300. As such, the film layer 20 may have a porosity less than a porosity of the foam base 22. In some examples, the film layer 20 comprises polysiloxane. In other examples, film layer 20 comprises polyurethane. The film layer may comprise alternative polymers as well.

The closure device 10 may include a phase-separated polymer having a porosity of greater than 50%. In a typical example, the stem portion 12 and the foam base 22 of the head portion 18 each include the phase-separated polymer. Of course, the stem portion 12 and the head portion 18 may include different phase-separated polymers. Further, if the stem portion 12 includes sub portions, these sub portions may include the same or different phase-separated polymers.

In other words, the phase-separated polymer in each particular portion may be different. For example, a first phase-separated polymer having lower porosity and more resilience may be used in the head portion 18 of the closure device 10 while a second phase-separated polymer having greater porosity and greater compressibility may be used to form the stem portion 12. In addition to the porosity, foam density establishes the physical properties of the particular portion. Porosity and foam density can be balanced to achieve good compressibility, which means that the foamed phase-separated polymer retains its structure (in particular its compression strength) when having absorbed or being saturated with a liquid, such as blood. The mechanical, structural and chemical properties of the foamed phase-separated polymer are mainly determined by the composition (structure) of polymer used. To this end, selection of the reactants used to form the phase-separated polymer provides a way to control and adjust the mechanical, structural and chemical properties of the phase-separated polymer.

The properties of the particular portions of the closure device 10 are, in many examples, tailored to swell (or not swell) upon exposure to moisture within the nasal cavity and inter cranial space. To this end, the stem portion 12 may be formed from a phase-separated polymer that is hydrophilic, while the head portion 18 and film layer 20 may be formed from a phase-separated polymer which is hydrophobic. Of course, the stem portion 12, the head portion 18, and the film layer 20 can be either hydrophilic or hydrophobic. In some configurations, poly(ethylene glycol) is avoided for use in the phase-separated polymer because swelling may increase the pressure within the cranial cavity 310 (intracranial pressure/ICP). As such, some examples of the closure device 10 include the head portion 18 and the film layer 20 which is less hydrophilic and relatively less porous than the stem portion 12. In other examples, the closure device 10 includes the head portion 18 and the film layer 20 which are extensively physically cross-linked, or have significant hydrogen bonding (e.g. polyurethane which is hydrogen bonded as is described below) and use low molecular weight poly(ethylene glycol).

The phase-separated polymer may be biodegradable or bioresorbable. The term "biodegradable" as used herein, refers to the ability of a polymer to be acted upon biochemically in general by living cells, organisms, or part of these systems, including hydrolysis, and to degrade and disintegrate into chemical or biochemical products. Further, the term "bioresorbable" as used herein, refers to the ability of being metabolized by the human or animal body.

The term "phase-separated polymer" as used herein, refers to a polymer comprising soft (amorphous) segments, as well as hard (crystalline) segments, the hard segment having a phase transition temperature of at least mammalian body temperatures (which is generally 37° C. for humans) and the phase-separated morphology being manifest when the foam prepared from such a polymer is applied in the human or animal body for a sufficient period of time. In addition, the polymer placed under temperature conditions comparable to the human or animal body exhibits the phase-separated morphology. A phase-separated polymer is characterized by the presence of at least two immiscible or partly miscible phases with a different morphology at normal environmental conditions. Within one material, a rubber phase and a crystalline phase (at a temperature above the glass transition temperature of the amorphous phase and below the melting temperature of the crystalline phase) may be present or a glassy and a crystalline phase (at a temperature below the glass transition temperature of the amorphous phase). Also at least two amorphous phases may be present at a temperature between the two phase transitions, e.g. one glassy and one rubbery phase. At a temperature above the highest phase transition, which is either a melting or glass transition temperature, the liquid and rubbery or the two rubbery phases, respectively, may form a phase mixed morphology or they may still be immiscible. Immiscible liquid and/or rubbery phases usually results in a polymer with a phase-separated morphology without the initial desired mechanical properties at normal environmental conditions.

In some examples, the phase-separated polymer has a porosity of greater than 50, 60, 70, or 80%. Alternatively, the phase-separated polymer has a porosity from 30 to 99%, from 40 to 99%, from 50 to 96%, from 60 to 96%, from 70 to 96%, from 80 to 93%, from 80 to 90%, from 80 to 87%, from 80 to 84%, from 83 to 99%, from 85 to 99%, from 89 to 99%, from 92 to 99%, from 95 to 99%, from 83 to 96%, from 86 to 93%, from 92-98%, or from 95-98%.

In some examples, the phase-separated polymer has a foam density of 0.01 to 1.0 g/cm$^3$. Alternatively, the foam density may be from 0.01 to 0.5, 0.01 to 0.3, 0.01 to 0.1, 0.01 to 0.09, 0.01 to 0.08, 0.01 to 0.07, 0.01 to 0.06, 0.01 to 0.05, 0.01 to 0.04, 0.01 to 0.03, 0.02 to 0.08, 0.04 to 0.08, 0.05 to 0.08, 0.06 to 0.08, 0.02 to 0.08, or 0.03-0.07 g/cm$^3$. In certain examples, the phase-separated polymer has a porosity of 85-99% and a foam density of 0.03-0.07 g/cm$^3$. It is to be appreciated that the term "foam density" as used throughout this disclosure refers to the density of foam, calculated as the phase-separated polymer mass per volume unit of particular foam portion. Accordingly, if the particular foamed portion includes an active agent, the mass of the active agent present in the particular foamed portion is disregarded when calculating the foam density.

The phase-separated polymer may be selected from the group consisting of polyesters, polyethers, polyhydroxyacids, polylactones, polyetheresters, polycarbonates, polydioxanes, polyanhydrides, polyurethanes, polyester(ether)urethanes, polyurethane urea, polyamides, polyesteramides, poly-orthoesters, polyaminoacids, polyphosphonates, polyphosphazenes and combinations thereof. Such polymers are described in WO 99/64491 A1, which is incorporated by reference in its entirety.

As is described above, the phase-separated polymer includes soft (amorphous) segments, as well as hard (crystalline) segments. The term "amorphous" as used herein, refers to segments present in the phase-separated polymer with at least one glass transition temperature below the temperature of the cavities of the human or animal body into which the foam is packed, and may also refer to a combination of an amorphous and crystalline segment which is completely amorphous when packed in the human or animal body. For example, PEG in a pre-polymer may be crystalline in pure form but may be amorphous when included in the R segment of a polyurethane of the formula (I). Longer PEG segments may also be partly crystalline when included in the R segment of a polyurethane of the formula (I) but will become amorphous ("dissolves") when placed in contact with water. Therefore, such longer PEG segments are part of the soft segment of the phase-separated polymer of the formulas (I), whereas the hard segment should remain crystalline in nature to provide sufficient support for a particular foamed portion in the wet and packed state for a certain period of time.

The term "crystalline" as used herein, refers to segments, present in the phase-separated polymer, that are crystalline when packed in the human or animal body, i.e., that have a melting temperature above the temperature of the human or animal body into which the closure device 10 is inserted.

A "hydrophilic segment" as used herein, refers to a segment comprising at least one, preferably at least two, more preferably at least three hydrophilic groups such as may be provided for instance by C—O—C, or ether, linkages. A polyether segment may thus provide a hydrophilic segment. A hydrophilic segment may also be provided by polypeptide, poly(vinyl alcohol), polyvinylpyrrolidone) or poly(hydroxyethylmethacrylate). A hydrophilic segment is preferably derived from polyalkyleneglycol, such as polyethyleneglycol, polypropyleneglycol, or polybutyleneglycol. The preferred hydrophilic segment is a polyethyleneglycol (PEG) segment.

The term "segment" as used herein, refers to a polymeric structure of any length. In the art of polymer technology, a long polymeric structure is often referred to as a block, whereas a short polymeric structure is often referred to as a segment. Both these conventional meanings are understood to be included in the term "segment" as used herein.

In one particular example of the present application, the phase-separated polymer is of the formula:

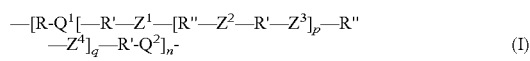

$$-[R-Q^1[-R'-Z^1-[R''-Z^2-R'-Z^3]_p-R''-Z^4]_q-R'-Q^2]_n- \qquad (I)$$

wherein R is selected from one or more aliphatic polyesters, polyetheresters, polyethers, polyanhydrides and/or polycarbonates, and optionally at least one R includes a hydrophilic segment, R' and R" are independently C2-C8 alkylene, optionally substituted with C1-C10 alkyl or C1-C10 alkyl groups substituted with halides or protected S, N, P or O moieties and/or comprising S, N, P or O in the alkylene chain, Z1-Z4 are independently amide, urea or urethane, Q1 and Q2 are independently urea, urethane, amide, carbonate, ester or anhydride, n is an integer from 5-500, p and q are independent 0 or 1, provided that when q is O, R is at least one amorphous aliphatic polyester, polyether, polyanhydride and/or polycarbonate segment with optionally at least one crystalline polyether, polyester, polyetherester or polyanhydride segment.

The simplest form of the phase-separated polymer, as represented by formula I, is of the formula: —R— $Q^1$-R'-$Q^2$—, i.e. when q=0.

The amorphous segment is included in the —R— part of the polymer according to formula (I). In case q=1, the $Q^1[-R'-Z^1-[R''-Z^2-R'-Z^3]_p-R''-Z^4]_q-R'-Q^2$ part of the polymer according to formula (I) represents the crystalline segment. In this particular example, the amorphous and crystalline segments are alternating, thus providing the hard segment with a uniform block-length.

As described above, R may represent a mixture of two or more different types of aliphatic polyesters, polyetheresters, polyethers, polyanhydrides and/or polycarbonates, which mixture includes both amorphous and crystalline types, so that both are included in a particular foamed portion. In the case that a mixture of amorphous and crystalline types of R segments are provided in a polymer according to the formula (I), optionally at least one hydrophilic segment is provided in at least one amorphous R segment.

R may in particular be derived from the cyclic monomers lactide (L, D or LD), glycolide, ε-caprolactone, δ-valerolactone, trimethylenecarbonate, tetramethylenecarbonate, 1,5-dioxepane-2-one, para-dioxanone, and combinations thereof and optionally polyethyleneglycol, polypropyleneglycol, polybutyleneglycol and combinations thereof. In certain examples, R is an amorphous polyester derived from exclusively lactide and ε-caprolactone, with a molecular weight between 1000 and 4000. In one example, R is about 25 wt. % lactide, about 25 wt. % ε-caprolactone and about 50 wt. % of polyethyleneglycol.

In a phase-separated polymer according to the formula (I), $Q^1$ and $Q^2$ may be selected from amide, urea, urethane ester, carbonate or anhydride groups, whereas $Z^1$ through $Z^4$ should be chosen from amide, urea or urethane groups so that at least 4 hydrogen bond forming groups are present in a row in the crystalline segment. The group R' in —$Z^2$—R'—$Z^3$— may be different or similar to R' in —$Q^1$—R'—$Z^1$— or —$Z^4$—R'—$Q^2$—.

As stated, R optionally includes a hydrophilic segment and such a hydrophilic segment may very suitably be an ether segment, such as a polyether segment derivable from such polyether compounds as polyethyleneglycol, polypropyleneglycol or polybutyleneglycol. Also, a hydrophilic segment included in R may be derived from polypeptide, poly(vinyl alcohol), polyvinylpyrrolidone) or poly(hydroxyethylmethacrylate). A hydrophilic segment is preferably a polyether, e.g. a poly(alkylkene glycol), such as poly(ethylene glycol), poly(propylene glycol) or poly (butylene) glycol.

In certain examples, the amorphous segment includes a hydrophilic segment. The hydrophilic segment may include polyethylene glycol in an amount of 1-80 wt %, more preferably 5-60 wt %, even more preferably 20-50 wt %, most preferably 50 wt %, based on the total weight of the hydrophilic segment.

In certain examples, the phase-separated polymer is a polymer according to formula I, wherein R' is $(CH_2)_4$, R" is $(CH_2)_4$, or both R' and R" are $(CH_2)_4$. For example, $Z^1$-$Z^4$ may be a urethane.

It should be appreciated that the foams described herein are comprised of a plurality of polymer chains, with each of the polymer chains comprising the phase-separated polymer, e.g. a polyurethane. In many examples, the foams are substantially free of any covalent cross-linking between polymer chains included in the foam. In the context of this disclosure, the term "substantially free of any covalent cross-linking" means that one polymer chain has less than 20, less than 10, less than 6, less than 4, or less than 2 covalent bonds to other polymer chains included in the foam. In some examples, the foam is free of any covalent cross-linking between polymer chains included in the foam. In other words, each polymer chain is not covalently cross-linked to any other polymer chain included in the foam.

In some preferred examples, the phase-separated polymer is a polyurethane foam including amorphous segments and crystalline segments, the crystalline segments formed via hydrogen bonding. In such examples, the crystalline segments include the reaction product of 1,4 butanediol and 1,4 diisocyanatobutane, while the amorphous segments in the polyurethane foam include a polyalkylene glycol, e.g. poly (ethylene glycol), a polyester, e.g. polyglycolide, or a combination of the two.

The term "hydrogen bonding" as used herein, refers to a partially electrostatic attraction between a hydrogen (H) atom which is bound to a more electronegative atom or group, such as nitrogen (N), oxygen (O), or fluorine (F)—the hydrogen bond donor—and another adjacent atom bearing a lone pair of electrons—the hydrogen bond acceptor. In polyurethanes, hydrogen bonding between carbonyl and N—H groups is one of the major driving forces for phase separation. Hydrogen bonds may be intermolecular (occurring between separate molecules) or intramolecular (occurring among parts of the same molecule).

In such examples, the foams described herein comprise hard/crystalline and soft/amorphous segments. The hard segments are formed via hydrogen bonding between urethane segments of each polymer chain. While not wishing to be bound by one particular theory, it is believed that urethane segments of each polymer chain are particularly susceptible to hydrogen bonding with other urethane segments in adjacent polymer chains. Accordingly, during formation of the foam, the urethane segments of each polymer chain are hydrogen bonded to, and thereby aligned with, the urethane segments of other polymer chains included in the foam. Because the urethane segments of each polymer chain are aligned with urethane segments of the other polymer chains, the polyetherester segments of each polymer chain are necessarily aligned with the polyetherester segments of other polymer chains included in the foam. The alignment of these polyetherester segments forms the soft segments of the foam. As such, because of the hydrogen bonding between urethane segments of each polymer chain, the foam exhibits a highly organized three-dimensional network structure of hard and soft segments.

Accordingly, the polyurethane foam of this preferred example includes crystalline segments formed via hydrogen bonding. Further, it is believed that the crystalline segments comprising the reaction product of 1,4 butanediol and 1,4 diisocyanatobutane and the amorphous segments comprising poly(ethylene glycol) form crystalline segments and the amorphous segments that "stack" in an alternating configuration to provide a 3-dimentional porous structure which is strengthened via hydrogen bonding between the stacked crystalline segments.

Further, the polyurethane foam of this preferred example readily interacts with other polymers to hydrogen bond because it includes the crystalline segments comprising the reaction product of 1,4 butanediol and 1,4 diisocyanatobutane and the amorphous segments comprising poly(ethylene glycol). As such, the film layer 20 may be selected from a polymer such as polyurethane or silicone such that the film layer 20 and the foam base 22 are bonded to one another via hydrogen bonding and substantially free of covalent bonds therebetween. In this example, hydrogen bonding between the phase-separated polymer comprising crystalline segments comprising the reaction product of 1,4 butanediol and 1,4 diisocyanatobutane and amorphous segments comprising poly(ethylene glycol), and the film layer 20 including silanol groups and/or urethane group occurs readily. Of course, hydrogen bonding between the film layer 20 and the foam base 22 eliminate the need for an adhesive therebetween. As such, in many examples, the bond interface 24 between the film layer 20 and the foam base 22 is free of adhesive.

In a typical example, the removal of the film layer 20 from the foam base 22 results in cohesive failure of the foam base 22 at the bond interface 24. The failure mode exhibited when the film layer 20 is removed from the foam base 22 may be classified as adhesive failure, where failure occurs at the bond interface 24 between the film layer 20 and the foam base 22, and cohesive failure, where the failure occurs within the foam base 22. As such, cohesive failure may be further described as a % area of the surface of the film layer 20 which retains phase-separated polymer (foam) from the foam base 22 bonded thereto when the film layer 20 is peeled from the foam base 22. As such, in some examples, the cohesive failure between the film layer 20 and the foam base 22 is greater than 50, 60, 70, 80, 90, or 95%. Alternatively, the cohesive failure is described as from 50 to 99%, from 50 to 96%, from 60 to 96%, from 70 to 96%, from 80 to 93%, from 80 to 90%, from 80 to 87%, from 80 to 84%, from 83 to 99%, from 85 to 99%, from 89 to 99%, from 92 to 99%, from 95 to 99%, from 83 to 96%, from 86 to 93%, from 92-98%, from 95-98%, or 90%. Removal of the film layer 20 from the foam base 22 may be accomplished manually (via hand peeling the film layer 20 off the foam base 22) or in accordance with standardized test methods such as ASTM D3330 or ASTM D903.

An active agent may be dispersed within the phase-separated polymer of the stem portion 12 and/or the head portion 18. Of course, the stem portion 12 and the head portion 18 may include different active agents. Further, if the stem portion 12 includes different sub portions, these sub portions may include different active agents. In some examples, one or more of the portions may be free of the active agent.

The various portions/films of the closure device 10 may each include the active agent or drug, be substantially free of the drug, or free of the drug. The term "substantially free" as used with reference to any of the active agents or drugs described herein may be defined as less than 5, 4, 3, 2, 1, 0.5, 0.1, 0.05, or 0.01 wt. %, based on a total weight of a particular portion or on a total weight of the closure device 10. The disclosure that contemplates "substantially free of" also encompasses "free of". As such, when the portions and/or closure device 10 are described as "substantially free of" something, e.g. a drug, this descriptive language can be narrowed to "free of".

The active agent may be located in the cell walls of the foamed phase-separated polymer. Alternatively, the active agent may be located within the voids of the foamed phase-separated polymer. When drugs are located within the cell walls of the pores, the porosity of the particular drug containing foamed portion influences the release rate of the active agent. The higher the porosity, the higher the rate of release and vice versa. Without wishing to be bound by theory, it is believed that an increased porosity results in an increased degradation rate of the phase-separated polymer and thereby an increased release rate. In other words, the degradation of the phase-separated polymer controls the release of the active agent.

The rate of release of the active agent from the phase-separated polymer may be expressed as the time required to release a certain amount of drug in a certain amount of time. Typically, 8 hours to 1.5 days are required to release 50% of the active agent from the foamed shell portion. In particular examples, it may be preferred that 50% of the active agent is released in a longer time, e.g. in 1 to 5 days. To release about 100% (e.g. more than 95%) of the active agent, a time of 4 to 14 days is generally preferred.

Typically, the active agent is a drug (i.e., any pharmaceutically active compound), an antibiotics, an anti-inflammatory agent, a, corticosteroid, a hemostatic agent, an anti-allergen, an anti-cholinergic agent, an antihistamine, an anti-infective, an anti-platelet, an anti-coagulant, an anti-thrombic agent, an anti-scarring agent, an anti-proliferative agent, a chemotherapeutic agent, an anti-neoplastic agent, a pro-healing agent, decongestant, a vitamin, a hyperosmolar agent, an immunomodulator, an immunosuppressive agent, or combinations thereof.

In a preferred example, the active agent includes a molecule including at least one hydrogen atom, which is bound to a nitrogen, oxygen, or fluorine atom. This structure facilitates hydrogen bonding between the active agent and phase-separated polymer, e.g. the polyurethane foam comprising the crystalline segments comprising the reaction product of 1,4 butanediol and 1,4 diisocyanatobutane and the amorphous segments comprising poly(ethylene glycol). In other words, the active agent may advantageously include a polymer that includes hydrogen atoms that are available to form a hydrogen bond with the crystalline segments of the first and/or second polyurethane foam. Hydrogen bonding between the active agent and the phase-separated polymer helps control and slow down the release of the active agent.

In one example, the active agent is a steroidal anti-inflammatory agent. It has been found that the relatively slow release of the active agent from the phase-separated polymer is particularly suitable for steroidal anti-inflammatory agents, such as corticosteroids.

In another example, the active agent is a hemostatic agent. Of course, the closure device 10 may include both an anti-inflammatory agent, e.g. a steroid, and a hemostatic agent. In various examples, the hemostatic agent includes at least one hydrogen atom bonded to a nitrogen atom, and/or at least one hydrogen atom bonded to an oxygen atom, with the hydrogen atoms being available to form a hydrogen bond with the crystalline segments of the first and/or second polyurethane foam. In such examples, molecules of the hemostatic agent and molecules of the phase-separated polymer are bonded to one another via hydrogen bonding and substantially free of covalent bonds therebetween.

In certain examples, the hemostatic agent is a chitosan hemostatic agent. The term "chitosan hemostatic agent" as used herein refers to chitosan or a salt or derivative thereof. Favorable results have been obtained using chitosan or chitosan acetate.

Chitosan is a polysaccharide comprising D-glucosamine units (deacetylated units) and N-acetyl-D-glucosamine units (acetylated units). Chitosan may be prepared from chitin by deacetylating at least part of the N-acetyl-D-glucosamine in chitin (poly-N-acetyl-D-glucosamine) by hydrolysis. The ratio of D-glucosamine units and N-acetyl-D-glucosamine units in chitosan is typically expressed as the degree of deacetylation. The degree of deacetylation is defined as the percentage of glucosamine units in chitosan that are not acetylated. This percentage thus corresponds to the molar percentage of deacetylated units present in chitosan.

Without being bound by theory, it is believed that a higher degree of deacetylation improves the hemostatic properties. The chitosan may have a degree of deacetylation of 1-100 mol %, 25-100 mol %, 50-100 mol %, 75-100 mol %, 85-100 mol %, 90-100 mol %, 5-50 mol %, 10-35 mol %, or 10-25 mol %. The above values also apply to chitosan present in chitosan salts, as well as to chitosan derivatives (which have acetylated and deacetylated units just like chitosan itself). In additional non-limiting examples, all values and ranges of degree of deacetylation values within and including the aforementioned range endpoints are hereby expressly contemplated. Without being bound by theory, it is believed that a higher degree of deacetylation improves the hemostatic properties of the chitosan.

Suitable chitosan salts are those with the chitosan ion having a net positive charge. Accordingly, suitable chitosan salts may be salts consisting of a chitosan cation and a counter anion. For example, the chitosan hemostatic agent may be a salt of chitosan with an organic acid, in particular with a carboxylic acid such as succinic acid, lactic acid or glutamic acid. Chitosan salts may for example be selected from the group consisting of nitrate, phosphate, glutamate, lactate, citrate, acetate and hydrochloride salts of chitosan.

In general, a chitosan derivative is a chitosan molecule wherein one or more of the hydroxyl groups and/or the amine group present in chitosan has been substituted. For example, the one or more hydroxyl groups may be substituted to obtain an ether or ester. The amine group may be substituted to obtain an amino group, although this generally results in a decrease in hemostatic activity. Therefore, the amine groups of chitosan are typically unsubstituted.

The chitosan hemostatic agent may include or be derived from chitosan originating from animals, plants or shellfish. These sources give similar good results with respect to the hemostatic effects described above. Furthermore, synthetic chitosan may also be used.

Further examples of suitable chitosan salts are chitosan esters of glutamate, succinate, phthalate or lactate, chitosan derivatives comprising one or more carboxymethyl cellulose groups, carboxymethyl chitosan. Other suitable examples of chitosan derivates are chitosan with quaternary groups (like N-trimethylene chloride, N-trimethylene ammonium). In addition, bioactive excipients such as calcitonin or 5-methylpyrrolidinone may be used.

The chitosan hemostatic agent may have a molecular weight in the range of about 1-1000 kDa, 1-500 kDa, 1-250 kDa, 1-100 kDa, 10-1000 kDa, 10-500 kDa, 10-250 kDa, 10-100 kDa, 30-80 kDa, 50-1000 kDa, 50-500 kDa, 50-350 kDa, 50-250 kDa, 100-1000 kDa, 100-750 kDa, 100-500 kDa, 100-250 kDa, 150-500 Kda, 200-1000 kDa, 200-750 kDa, 200-500 kDa, 225-275 kDa, 200-300 kDa, 210-390 kDa, 90-1000 kDa, 190-1000 kDa, 290-1000 kDa, or 390-1000 kDa. In additional non-limiting examples, all values and ranges of molecular weight values within and including the aforementioned range endpoints are hereby expressly contemplated.

In certain examples, when the active agent is the hemostatic agent, the foamed portion including the hemostatic agent (i.e., the foamed shell portion and/or the foamed core portion) has a porosity of 35-99%, or 85-99% and a foam density of 0.03-1.1, or 0.03-0.07 $g/cm^3$. Such values for the porosity and density contribute to the enhanced hemostatic activity and also provide the foam with good liquid (e.g. water or blood) absorbing properties. Alternatively, the foamed portion has a porosity of 92-98%, or 95-98% and a foam density of 0.03-0.07 $g/cm^3$.

The amount of hemostatic agent may be at least 0.1 wt. %, preferably at least 2 wt. %, more preferably at least 5. wt. % of the total weight of the foam portion comprising the hemostatic agent. Notably, even this relatively small amount of hemostatic agent is sufficient to provide the foam nasal dressing with desirable hemostatic properties. Furthermore, the amount of hemostatic agent is generally less than 99 wt. %, less than 50 wt. %, or less than 35 wt. % of the total weight of the foam portion. Since the hemostatic activity of the foam nasal dressing is almost independent on hemostatic agent, high concentrations are generally neither required nor preferred.

The hemostatic agent is preferably present in the foam in the form of particles, in particular polymeric particles. Examples of suitable particles are amorphous, crystalline and gel-like particles. The hemostatic agents may also be liquid, in particular when highly viscous. In case of hemostatic particles, the particles may have a size from 1-1000 μm. Preferably, particles are smaller than 150 μm. In particular good results have been obtained using particles of 5-90 μm. Small particles have a number of advantages. First, the structure of the foam is less influenced by the presence of small particles than large particles. Second, small hemostatic particles have a smaller tendency to aggregate than large particles. Furthermore, a good dispersion may be obtained using small particles. Lastly, small particles do not settle down when preparing the foam, such that a homogeneous distribution within the foam may be achieved if desirable.

The hemostatic particles may be any suitable shape, but are preferably roughly spherical. The particles are preferably solid. Suitable solid particles to be used are generally insoluble and hydrophilic.

The present disclosure also includes a method of making the closure device 10. In a typical example, the closure device 10 may be formed via a phase separation method. That is, in some examples, phase separation of a polymer solution may be used to produce a polymer-rich domain and a solvent-rich domain, and this morphology may be fixed by quenching under low temperature conditions. Removal of solvent through freeze-drying or extraction produces the phase-separated polymer. Phase separation may be induced by changing the temperature or by adding non-solvent to the polymer solution. In polyurethanes, hydrogen bonding between carbonyl and N—H groups is one of the major driving forces for phase separation.

In one example, the method of forming the closure device 10 having the head portion 18 and the stem portion 12 includes the step of providing a mold defining a void space for forming the head and stem portions 12, 18; placing a first liquid comprising a phase-separated polymer in the mold; cooling the first liquid to freeze the first liquid; and drying the first liquid to form the closure device 10.

In another example, the method of forming the closure device 10 having the head portion 18 and the stem portion 12 includes the step of providing a mold defining a void space for forming the head and stem portions 12, 18; providing a spacer; placing the spacer at least partially into the mold; placing a first liquid comprising a first phase-separated polymer in the mold; cooling the first liquid to freeze the first liquid; removing the spacer from the frozen first liquid to form a secondary void space; placing a second liquid in the secondary void space; cooling the second liquid to freeze the second liquid; and drying the first and second liquids to form the closure device 10.

The method may further include the step of placing the film layer 20 over the first and or second liquids prior to the step(s) of freezing, after the step(s) freezing, or after the step(s) of drying.

The mold and/or the spacer may have a cavity of any suitable shape and/or size. The mold and/or spacer may be formed from any suitable material. In examples where the closure device 10 includes one or more phase-separated polymers, the method may further include placing a spacer in the mold. Although the shape of the spacer is not particularly limited, the shape should prevent the spacer from reaching the bottom of the cavity of the mold and should cooperate with the mold to be suspended in the void space as desired.

The method further includes placing a first and/or a second liquid in the mold. The first liquid may include the first phase-separated polymer, a solvent, and optionally the active agent. The second liquid may include the second phase-separated polymer (which may be the same as the first phase-separated polymer), a solvent, and optionally the active agent. When solvent is included, the first and/or second liquid suitable solvents include polar solvents which have freezing points in the range of about 0-50° C. Such solvents may be removed by drying. Such suitable solvents include organic solvents such as acetic acid, benzene, cyclohexane formic acid, nitrobenzene, phenol, 1,4-dioxane, 1,2,4-trichlorobenzene, dimethylsulphoxide (DMSO) and combinations thereof. In one example, the solvent used is 1,4-dioxane. When the first and/or second liquid includes a solvent, the first liquid is typically formed by dissolving the first phase-separated polymer and the active agent in the solvent. Of course, the spacer and the first liquid may be placed in the mold in any order. When in the mold, the first liquid and the spacer are in contact. In other words, the spacer displaces at least a portion of the volume of the first liquid in the mold.

The method further includes cooling the first liquid to freeze the first liquid. The cooling of the first liquid may be carried out at any suitable temperature capable of freezing the first liquid. If the step of freezing the second liquid is also included, the cooling of the second liquid may be carried out at any suitable temperature capable of freezing the second liquid.

The method further includes removing the spacer from the frozen first liquid to expose a cavity in the frozen first liquid. To facilitate removal of the spacer from the frozen first liquid, the spacer is typically formed of PTFE and generally cylindrically shaped. PTFE is advantageous due to its inherent low frictional properties. In addition, using a generally cylindrically shaped spacer or spacer having an arcuate surface allows the spacer to be "spun" while being removed to loosen the spacer from the frozen first liquid without disrupting the physical shape of the frozen first liquid.

In certain examples, drying is performed by lowering the pressure and increasing the temperature such that any solvent present in first and second frozen liquids is sublimed from the phase-separated polymers. In some examples, the temperature increase may be in part from the latent heat of sublimation of solvent molecules and may result in up to 90%, 95%, or 100% of the solvent subliming. The entire freeze-drying process may last from about 0.5 hour to 24 hours, or more.

In certain examples, when the active agent is not soluble in the phase-separated polymer or solvent, the method includes additional steps to ensure a homogeneous incorporation of the active agent into the particular foam portion. When the active agent is not soluble in the phase-separated polymer and/or solvent, the active agent is typically a particle.

Figure 5:
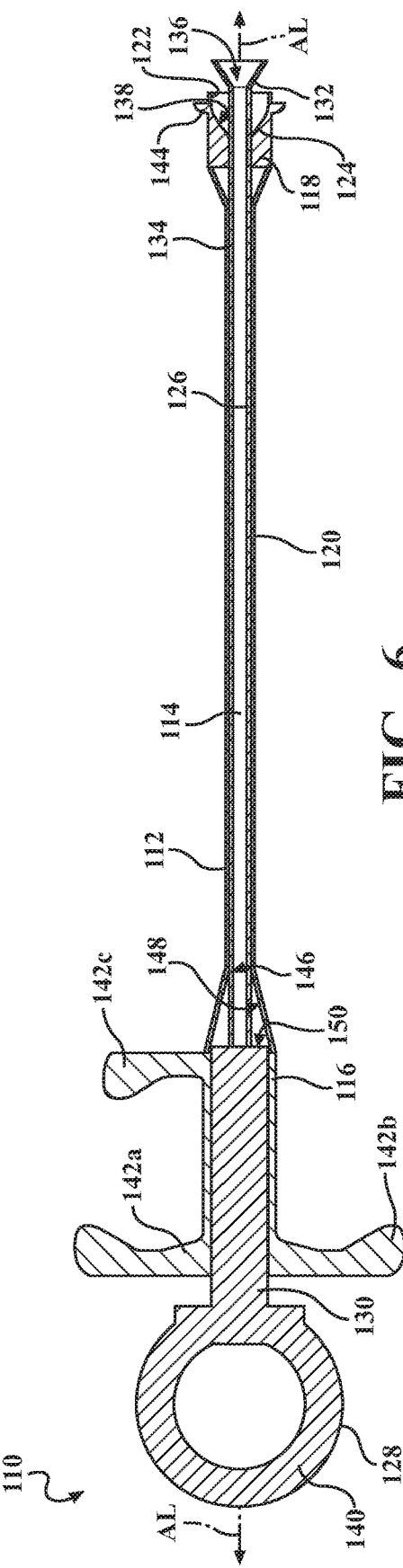
FIG. 5 is a perspective view of an exemplary surgical tool for placing the closure device in an opening in a base of a skull.
Figure 6:
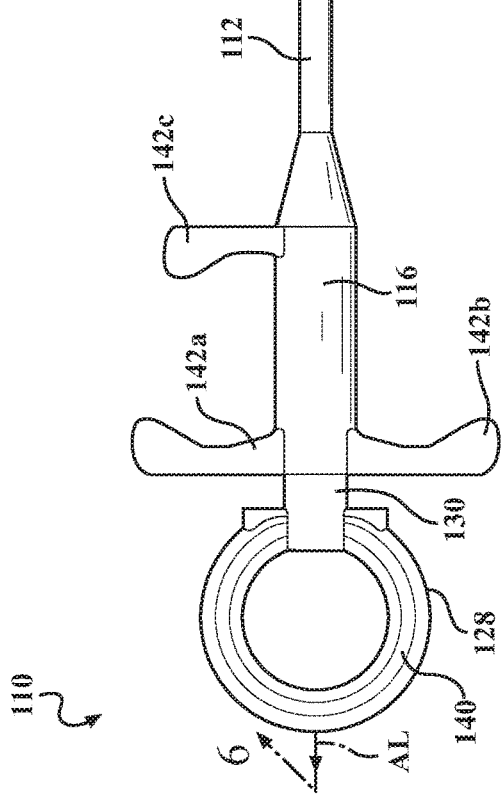
FIG. 6 is a cross-sectional view along 6-6 of the surgical tool of FIG. 5.

The present disclosure also includes a surgical tool 110 for trans-nasally placing the closure device 10 in an opening 300 in the skull 302. Referring now to FIGS. 5 and 6, the surgical tool 110 includes a body 112 defining an inner channel 114, the body 112 having a handle 116, a dispensing tip 118, and a central section 120 therebetween. The dispensing tip 118 has a tapered profile between a first region 122 and a second region 124, the first region 122 having a greater diameter $D_{122}$ than the second region $D_{124}$. Alternatively, the dispensing tip 118 may be described as having a flared portion which includes the first region 122 and a second region 124. The flared portion has an inner diameter, which increases along the longitudinal axis $A_L$ in a radial direction. A shaft 126 is moveably disposed in the inner channel 114 of the body 112, the shaft 126 has a control surface 128 at a proximal region 130 and a deformable head 132 at a distal region 134, the shaft 126 and the deformable head 132 cooperate to define a lumen 136 to accommodate a portion of the closure device 10.

Referring now to FIGS. 7 and 8, upon actuation of the control surface 128, the deformable head 132 moves between a first state in which the deformable head 132 is outside of the second region 124 of the dispensing tip 118 and a second state where the deformable head 132 is at least partially within the second region 124 of the dispensing tip 118, wherein a diameter of the deformable head 132 in the first state is greater than a diameter of the deformable head 132 in the second state.

In a typical example, the deformable head 132 is conical when not deformed. The deformable head 132 may have an inner surface with a higher coefficient of friction which allows the head to grip onto the closure device 10 during loading, and an outer surface with a lower coefficient of friction so that the deformable head slides easily into the lumen of the dispensing tip. The surface characteristics of the inner and outer surfaces of the deformable head 132 can be obtained by using a multilayer head with different materials defining the inner and outer surfaces of the deformable head 132. Alternatively, various spray coatings can be used to increase or decrease the lubricity or "grip" provided by the particular surface. In some examples, the inner surface of the deformable head 132 is patterned, e.g. with bumps or ridges, to improve its grip on the closure device 10 during loading of the closure device 10 into the surgical tool 110.

Still referring to FIGS. 7 and 8, the dispensing tip 118 includes a sidewall 138 that defines a void having a tapered profile, and wherein, upon actuation of the control surface 128, the shaft 126 is moveable within the inner channel 114 to move the deformable head 132 proximally such that the sidewall 138 of the dispensing tip 118 engages the stem portion 12 and deforms the head portion 18 to load the closure device 10 into the surgical tool 110.

In FIG. 7B, the closure device 10 is in a free state FS and the head portion 18 has a diameter DF. In FIG. 8B, the closure device 10 is in a deformed state DS and the head portion 18 has a diameter DD that is less than the diameter DF. This allows for insertion of the closure device into the opening 330 having a diameter which is smaller than the diameter DF of the head portion 18 in the free state FS.

Still referring to FIGS. 7 and 8, when the deformable head 132 is pulled proximally into the lumen 136 of the dispensing tip 118, the deformable head 132 deforms. As such, the deformable head 132 typically comprises a thermoplastic, a thermoplastic elastomer, or an elastomer. When the deformable head 132 is pulled proximally into the lumen 136 of the dispensing tip 118, the closure device 10 likewise deforms. In a typical example, the stem portion 12 and the head portion 18 of the closure device 10 are compressed. Furthermore, the head portion 18 may be deformed, collapsed, folded and/or compressed along the longitudinal axis $A_L$ in a distal direction. In other words, as the deformable head 132 and the closure device 10 are pulled proximally into the lumen 136 of the dispensing tip 118 along the longitudinal axis $A_L$, the stem and head portions 12, 18 are being compressed and the head portion 18 is being collapsed distally along the longitudinal axis $A_L$.

Still referring to FIGS. 7 and 8, the control surface 128 includes a thumb stirrup 140 and a plurality of finger saddles 142. In this example, there are three finger saddles 142a, 142b, and 142c. A user may insert their thumb into the thumb stirrup 140 and loop their index and middle fingers over the finger saddles 142a, 142b, and 142c and actuate the surgical tool 110 with only one hand. Finger saddle 142c allows for single-handed actuation in a proximal direction to load the closure device 10, while finger saddles 142a, 142b allow for single-handed actuation in a distal direction to release the closure device 10.

In a typical example, the dispensing tip 118 is formed separately from the central section 120 and is coupled thereto. In other examples, the dispensing tip 118 and the central section 120 are integral. The dispensing tip 118 is typically conical. Further, the dispensing tip 118 includes an alignment flange 144, wherein the alignment flange 144 is configured to rest on an outer surface 306 of the skull 302. That is, the alignment flange 144 rests on the outer surface 306 of the skull 302 when the dispensing tip 118 is inserted into the opening 300 such that the closure device 10 is positioned in the opening 300 and does not penetrate too far into a cranial cavity 310.

Figure 9:
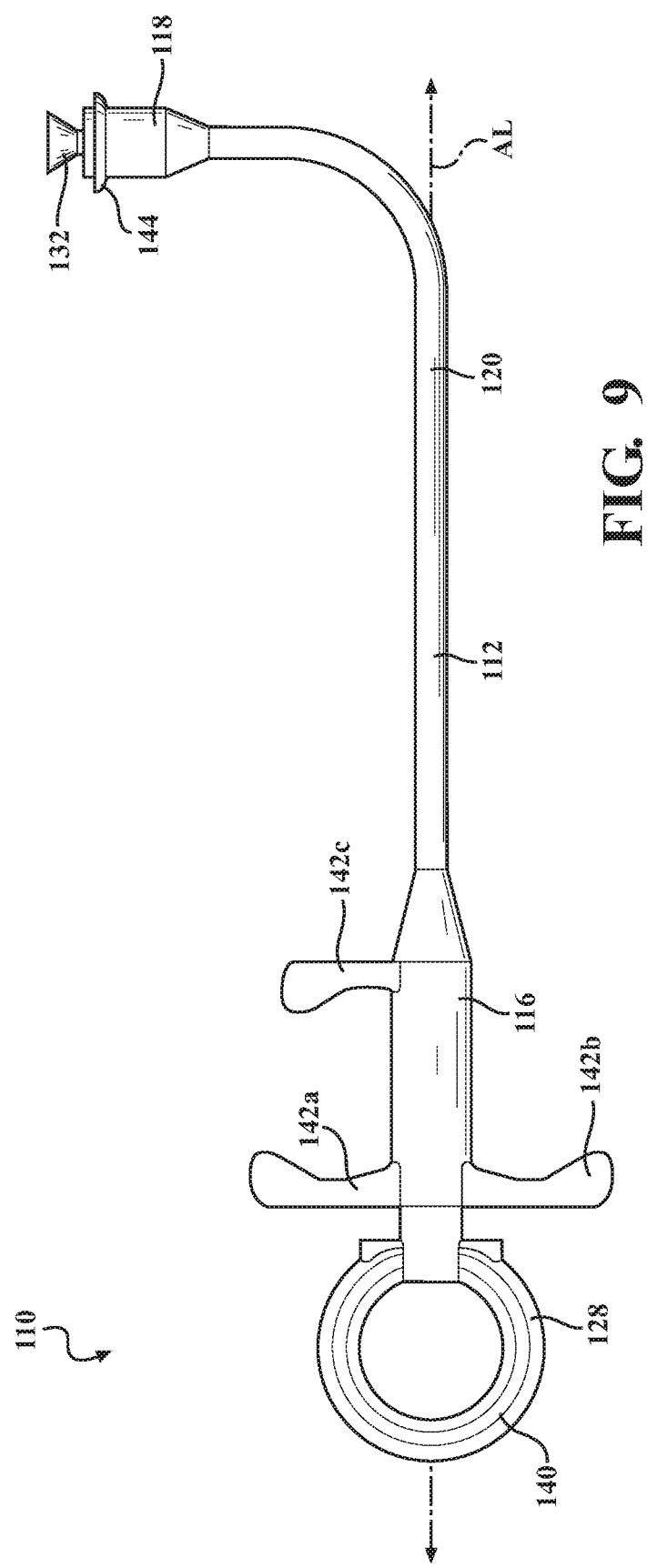
FIG. 9 is a perspective view of another exemplary surgical tool for placing a closure device in an opening in a base of a skull, the surgical tool having a flexible central section that allows a shape of the surgical tool to be changed to facilitate use of the surgical tool in a nasal cavity.

Referring now to FIG. 9, in some examples, the surgical tool 110 includes the body 112 with the central section 120 comprising a malleable material, and the shaft 126 (not shown in FIG. 9) includes a flexible material such that a shape of the surgical tool 110 may be changed to facilitate use of the surgical tool 110 in the nasal cavity 298. In FIG. 9, the surgical tool 110 has a curved shape to facilitate its use in the nasal cavity 298.

Referring back to FIG. 6, the body 112 of the surgical tool 110 has an inner surface 146 which defines the inner channel 114 and also a stop surface 148, wherein the shaft 126 includes a stop shelf 150 extending radially therearound. The stop shelf 150 cooperates with the stop surface 148 to stop movement of the shaft 126 along a longitudinal axis $A_L$ in the distal direction.

The surgical tool 110 may, in many examples, be sterilized, e.g. autoclaved, and reused. That is, the materials used to form some examples of the surgical tool 110 may withstand elevated temperature and humidity. In other examples, the surgical tool 110 is disposable, and may be discarded after use.

The present disclosure also includes a system for trans-nasally closing the opening 300 in the base of the skull 302. The system includes the closure device 10 for trans-nasally closing an opening 300 in a base of the skull 302 and the surgical tool 110 for trans-nasally placing the closure device 10 in an opening 300 in the skull 302, both of which are described in detail above. The system may be packaged and sold as a kit, with the kit including the surgical tool 110 and one or more of the closure device 10. Of course, the one or more of the closure device 10 can be packaged with, sub-packaged with, or packaged independently of the kit. The system may also include a supplemental kit which includes one or more of the closure device 10 since, in many examples, the surgical tool 110 is designed to be sterilized, e.g. autoclaved, and reused.

The present disclosure also includes a method 500 of trans-nasally closing the opening 300 in the base of the skull/cranium 302 having the inner surface 304 defining the cranial cavity 310 with the closure device 10 (the closure device 10 is described in detail above). The method 500 of trans-nasally closing the opening 300 in the base of the skull/cranium 302 having the inner surface 304 defining the cranial cavity 310 with the closure device 10 in generally shown in FIG. 16. The method includes the step 502 of providing the closure device 10. At least the head portion 18 of the closure device 10 is deformed from a free shape to a deformed shape in step 504. Once deformed, in step 506 the head portion 18 is inserted through a nasal cavity 298 and through the opening 300 such that the head portion 18 is in the cranial cavity 310 and the stem portion 12 extends through the opening 300 and into the nasal cavity 298. Once released, in step 508 such that the closure device 10 at least partially reverts back to the free shape such that the stem portion 12 fills the opening 300 and the head portion 18 abuts the inner surface 304 of the skull/cranium 302 as well as dura 308, thereby securing the closure device 10 in position and sealing the opening 300.

In addition to the step 502 of providing the closure device 10, the method 500 may further include the step 510 of providing the surgical tool 110 for closing the opening 300 in the skull/cranium 302 with the closure device 10. The surgical tool 110 is just as previously described.

As set forth above, the method 500 includes the step 504 of deforming the closure device 10 from a free shape to a deformed shape is illustrated in FIGS. 7A, 7B, 8A, and 8B. In FIGS. 7A and 7B, the closure device 10 is un-deformed in a free state. In FIGS. 8A and 8B, the closure device 10 is deformed, for example, the head portion 18 of the closure device 10 is folded along the longitudinal axis $A_L$. It should be appreciated, that the step 504 of deforming the head portion 18 of the closure device 10 from a free shape to a deformed shape may comprise folding, as described above, or other means of deformation such as compression. For example, the step 504 of deforming the closure device 10 from a free shape to a deformed shape may comprise compressing the head portion 18 and stem portion 12 of the closure device 10, which is possible because the closure device 10 is foamed. As another example, the stem portion 12 and the head portion 18 can be compressed and the with the head portion 18 of the closure device 10 can also be collapsed or folded along the longitudinal axis $A_L$. Once compressed, the closure device 10 may be inserted in position and released in step 508 such that the closure device 10 at least partially reverts via expansion back to the free shape such that the stem portion 12 fills the opening 300 and the head portion 18 abuts the inner surface 304 of the skull/cranium 302 as well as dura 308, thereby securing the closure device 10 in position and sealing the opening 300. In the examples illustrated, the step 504 of deformation involves both folding and compression of the closure device 10.

It is to be appreciated that deformation can involve collapsing, folding, and/or compressing the closure device 10. Although not illustrated, the stem portion 12 of the closure device 10 can be compressed up to 10, 20, 30, 40, 50, 60, or 70% by volume, e.g. in the dispending tip 118 of the surgical tool 110, during deformation. As such, the release of the closure device 10 can cause the stem portion 12 substantially fill, or completely fill the opening 300. The head portion 18 is often collapsed or folded along the longitudinal axis $A_L$ and is, during the deformation process compressed too. In a typical example, the closure device 10 expands out into and fills the opening. Of course, the closure device 10 starts out in a first, undeformed state, and then is compressed into a second, compressed state. On release, the closure device 10 at least partially reverts back to its uncompressed shape. In many examples, the closure device 10 does not totally revert back to its original uncompressed state due to the anatomical features of the particular patient and other factors.

When the method 500 utilizes the surgical tool 110, the method 500 may further include the step of loading the closure device 10 into the surgical tool 110. The step of loading the closure device 10 in the surgical tool 110 is illustrated in FIGS. 7A, 7B, 8A, and 8B. FIG. 7A is the perspective view of the closure device 10 and the surgical tool 110 prior to loading the closure device 10 in the surgical tool 110, and FIG. 7B is cross-sectional view of the closure device 10 and a distal end of the surgical tool 110 prior to loading. Whereas FIG. 8A is a perspective view of the closure device 10 loaded into a distal end of the surgical tool 110, and FIG. 8B is a cross-sectional view of the closure device 10 loaded into the dispending tip 118 of the surgical tool 110. In such examples, the step 504 of deforming is further defined as moving the deformable head 132 proximally such that the dispensing tip 118 on the surgical tool 110 engages and deforms the stem portion 12 and the head portion 18 to load the closure device 10 into the surgical tool 110. Loading may be accomplished via a step of actuating a shaft on the surgical tool 110 from a disengaged position (shown in FIGS. 7A and 7B) to an engaged position (shown in FIGS. 8A and 8B) to deform the closure device 10 from a free shape to a constricted shape and load the closure device 10 within the dispensing tip 118. In some examples, the closure device 10 is compressed during the step 504 of deformation (and thus expands during the step 508 of releasing).

Prior to or after loading, the method 500 may include the step of bending the central section 120 of the surgical tool 110 to facilitate use of the surgical tool 110 in the nasal cavity 298. In FIG. 9, the surgical tool 110 has a curved shape to facilitate its use in the nasal cavity 298.

Figure 10:
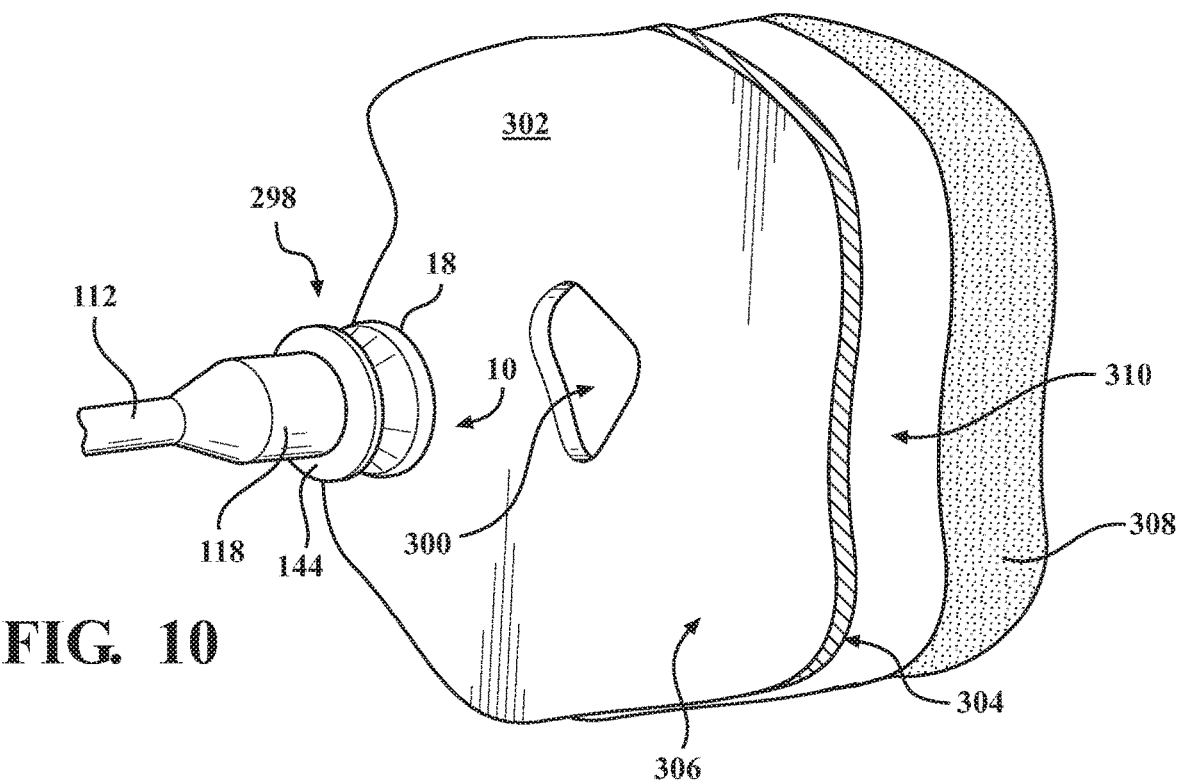
FIG. 10 is a perspective view of the closure device loaded into the surgical tool as well as an opening in a base of a skull.
Figure 11:
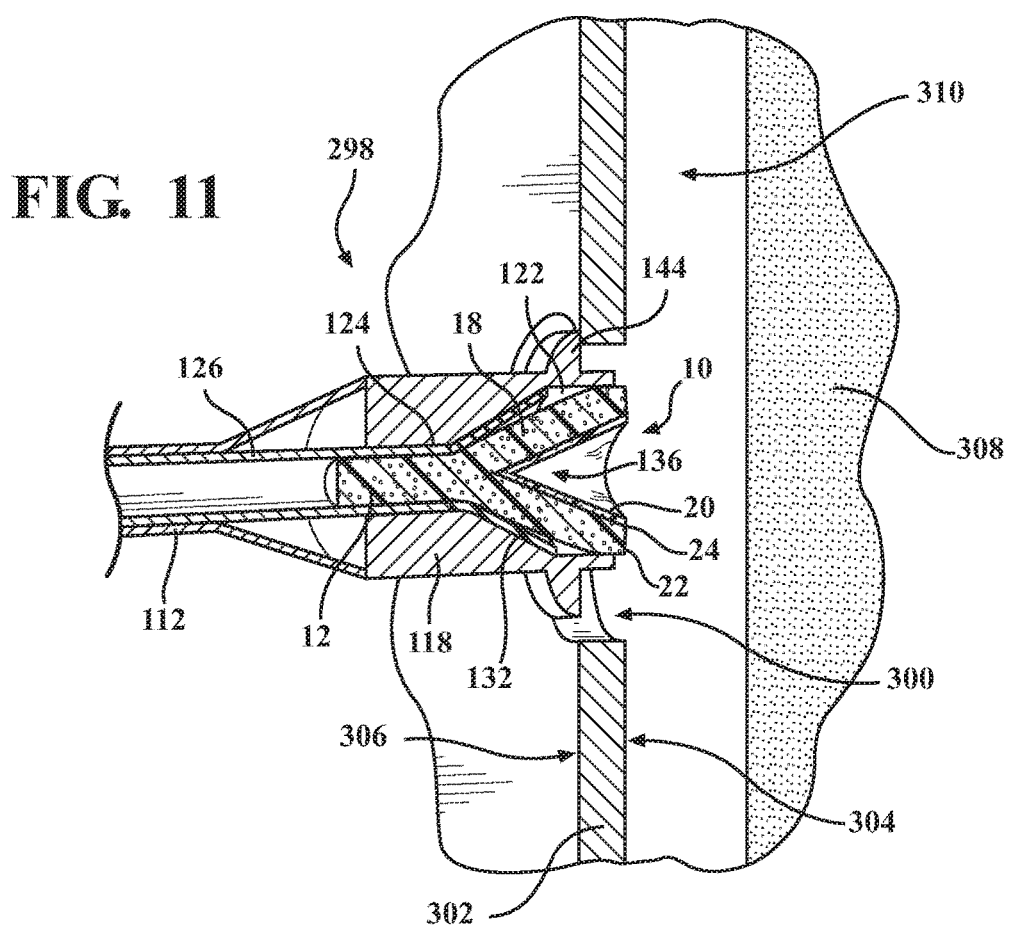
FIG. 11 is a cross-sectional view of the deformed closure device loaded into a surgical tool, which is aligned with and partially in the opening in the base of the skull.

Referring now to FIGS. 10 and 11, when the method 500 utilizes the surgical tool 110, the surgical tool 110 having the closure device loaded into the dispensing tip 118 is inserted into the nasal cavity 298 and the deformed head portion 18 of the closure device 10 extended through the nasal cavity 298 and into the opening 300 such that the head portion 18 of the closure device 10 is in the cranial cavity 310 and the stem portion 12 of the closure device 10 extends through the opening 300 and into the nasal cavity 298. FIG. 10 is a perspective view of the closure device 10 loaded into the surgical tool 110 as well as the opening 300 in a base of the skull 302, while FIG. 11 is a cross-sectional view of the deformed closure device 10 loaded into the surgical tool 110, which is aligned in the opening 300 in the base of the skull 302.

Figure 12:
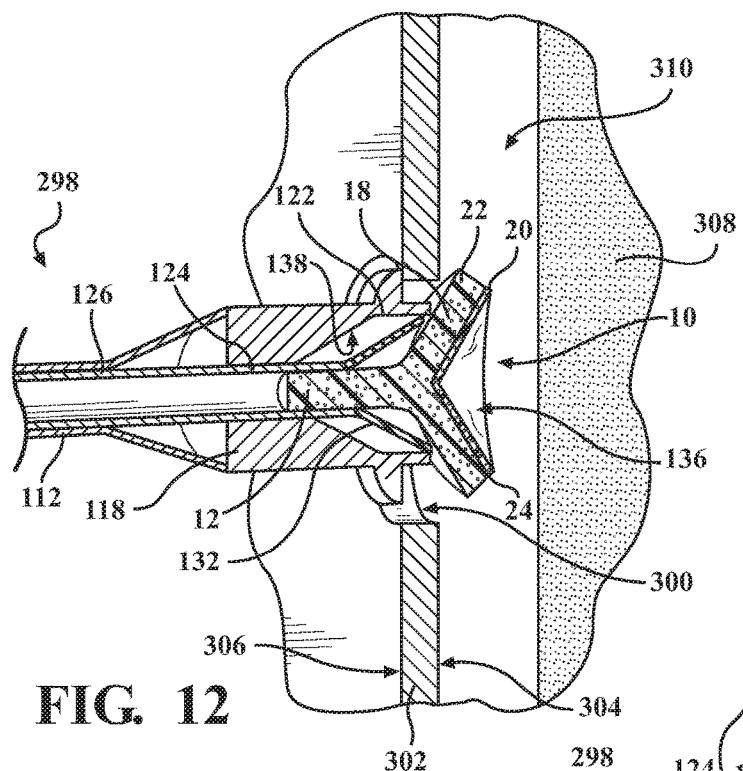
FIG. 12 is a cross-sectional view of the surgical tool inserted in the opening in the base of the skull with the deformed closure device partially released from the surgical tool.
Figure 13:
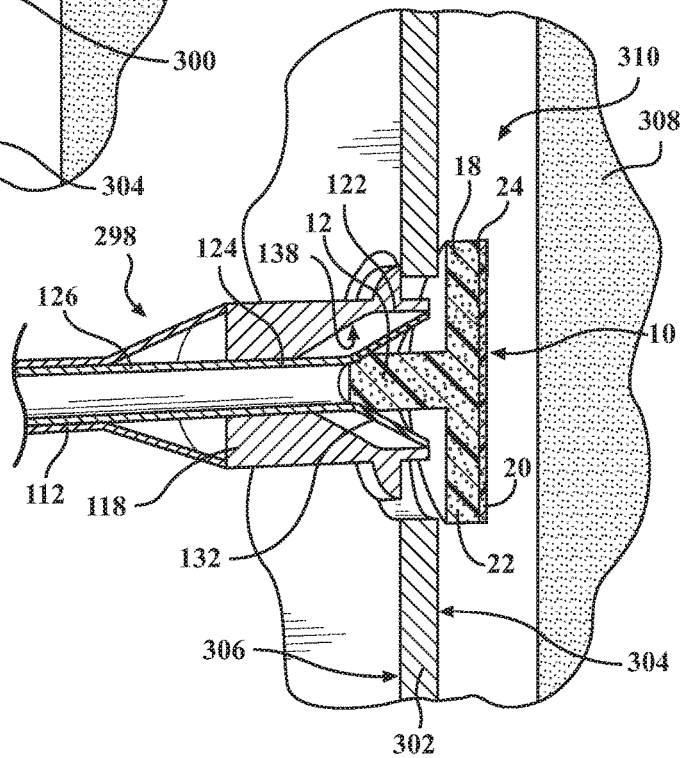
FIG. 13 is a cross-sectional view of the surgical tool inserted in the opening in the base of the skull with the deformed closure device fully released from the surgical tool.
Figure 14:
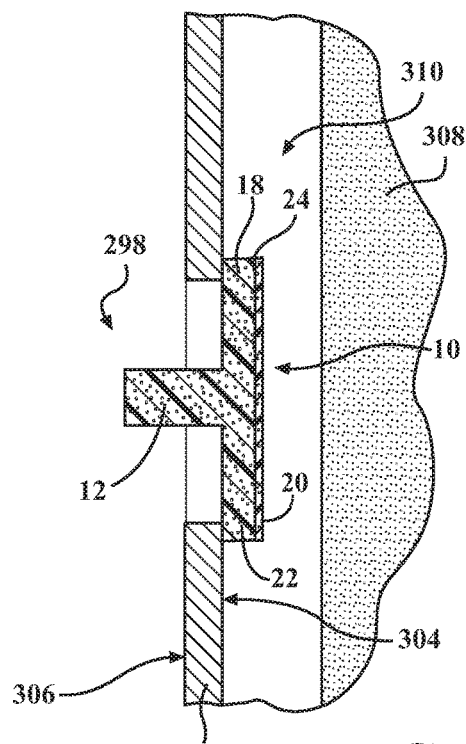
FIG. 14 is a cross-sectional view of the released closure device at least partially reverted back to its free shape such that the stem portion fills the opening and the head portion abuts an inner surface of the cranium as well as dura, thereby securing the closure device in position and sealing the opening.
Figure 15:
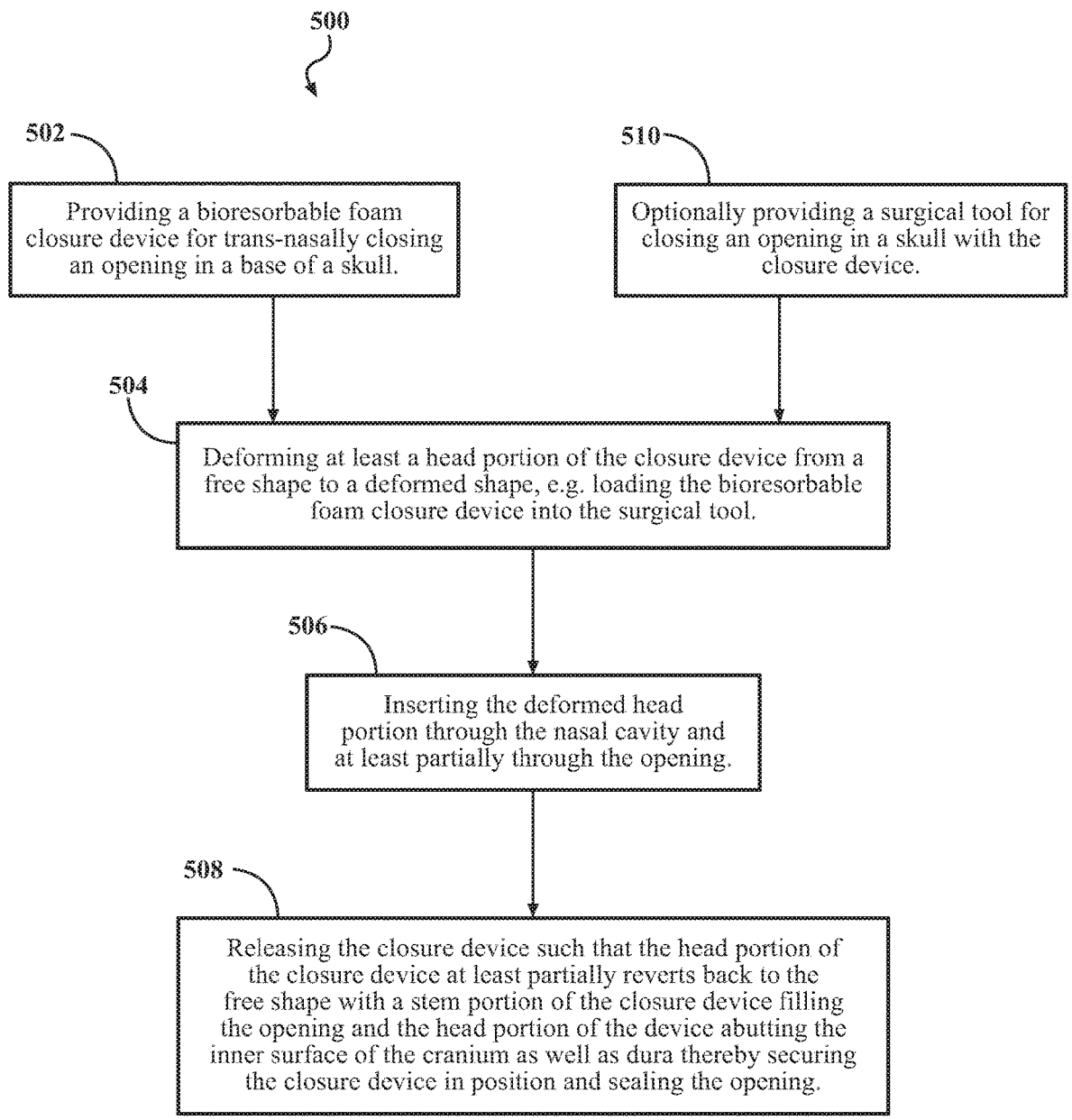
FIG. 15 is a flow diagram generally illustrating steps included in a method of trans-nasally closing the opening in the base of the skull/cranium with the closure device.

Referring now to FIGS. 12-14, the shaft 126 may be actuated from an engaged position to a disengaged position to release the closure device 10 in the opening 300. In FIG. 12, a cross-sectional view of the surgical tool 110 and the closure device 10 deformed and partially released in the opening 300 in the base of the skull 302 is illustrated and in FIG. 13 a cross-sectional view of the surgical tool 110 and the closure device 10 fully released in the opening 300 in the base of the skull 302 is illustrated. FIG. 14 is a cross-sectional view of the closure device 10 released and at least partially reverted back to its free shape such that the stem portion 12 fills the opening 300 and the head portion 18 abuts an inner surface 304 of the skull/cranium 302 as well as dura 308, thereby securing the closure device 10 in position and sealing the opening 300.

Additional Formatted Disclosure: Surgical Tool

I. A surgical tool for trans-nasally placing a bioresorbable foam closure device in an opening in a base of a skull, the closure device having a stem portion and a head portion, the surgical tool comprising:

a body defining an inner channel, the body having a handle, a dispensing tip, and a central section therebetween, the dispensing tip having a tapered profile between a first region and a second region, the first region having a greater diameter than the second region; and a shaft moveably disposed in the inner channel of the body, the shaft having a control surface at a proximal region and a deformable head at a distal region, the shaft and the deformable head cooperate to define a lumen to accommodate a portion of the closure device;

wherein upon actuation of the control surface, the deformable head moves between a first state in which the deformable head is outside of the second region of the dispensing tip and a second state where the deformable head is at least partially within the second region of the dispensing tip, wherein a diameter of the deformable head in the first state is greater than a diameter of the deformable head in the second state.

II. The surgical tool as set forth in II. wherein the dispensing tip includes sidewalls that define the tapered profile, and wherein upon actuation of the control surface the shaft moves proximally within the inner channel and the head moves proximally such that the sidewalls of the dispensing tip engage and deform the deformable head to load the closure device into the surgical tool.

III. The surgical tool as set forth in claim I. or II. wherein the control surface comprises a thumb stirrup.

IV. The surgical tool as set forth in claim III. wherein the control surface comprises a pair of finger saddles such that a user may insert their thumb into the thumb stirrup and loop their index and middle fingers over the finger saddles and actuate the surgical tool with one hand.

V. The surgical tool as set forth in any one of I. through IV. wherein the dispensing tip is formed separately from the central section and is coupled thereto.

VI. The surgical tool as set forth in any one of I. through V. wherein the dispensing tip comprises an alignment flange, wherein the alignment flange is configured to rest on an outer surface of the skull when the deformable head is inserted into the opening such that the closure device is positioned in the opening and does not penetrate too far into a cranial cavity.

VII. The surgical tool as set forth in any one of I. through VI. wherein the central section of the body comprises a malleable material, and the shaft comprises a flexible material such that a shape of the surgical tool may be changed to facilitate use of the surgical tool in a nasal cavity.

VIII. The surgical tool as set forth in any one of I. through VII. wherein the body has an inner surface which defines the inner channel and also a stop surface, wherein the shaft includes a stop shelf extending radially thereabout that cooperates with the stop surface to stop movement of the shaft along a longitudinal axis in the distal direction.

IX. The surgical tool as set forth in any one of I. through IIX. wherein the dispensing tip is conical.

X. The surgical tool as set forth in any one of I. through IX. wherein the deformable head is conical when not deformed.

Additional Formatted Disclosure: Closure Device

I. A bioresorbable foam closure device for trans-nasally closing an opening in a base of a skull, the device comprising:

a stem portion having a proximal end and a distal end, the stem having a first diameter; and a head portion at the distal end having a second diameter being larger than the first diameter;

wherein the head portion comprises a film layer and a foam layer, wherein a porosity of the film layer is greater than a porosity of the foam layer;

wherein the film layer is disposed at a distal end of the closure device and the foam layer of the head is disposed between the film layer and the stem portion;

wherein the head portion and the stem portion comprise a phase-separated polymer having a porosity of greater than 80%, the phase-separated polymer having the formula:

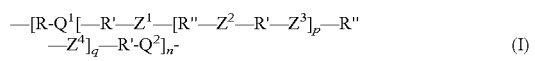

$$-[R-Q^1[-R'-Z^1-[R''-Z^2-R'-Z^3]_p-R''-Z^4]_q-R'-Q^2]_n- \quad (I)$$

wherein R is selected from one or more aliphatic polyesters, polyetheresters, polyethers, polyanhydrides and/or polycarbonates, and optionally at least one R comprises a hydrophilic segment, R' and R" are independently $C_2$-$C_8$ alkylene, optionally substituted with $C_1$-$C_{10}$ alkyl or $C_1$-$C_{10}$ alkyl groups substituted with halides or protected S, N, P or O moieties and/or comprising S, N, P or O in the alkylene chain, $Z^1$—$Z^4$ are independently amide, urea or urethane, $Q^1$ and $Q^2$ are independently urea, urethane, amide, carbonate, ester or anhydride, n is an integer from 5-500, p and q are independent 0 or 1, provided that when q is 0, R is at least one amorphous aliphatic polyester, polyether, polyanhydride and/or polycarbonate segment with optionally at least one crystalline polyether, polyester, polyetherester or polyanhydride segment;

wherein the closure device is deformed from a free shape to a constricted shape, inserted through a nasal cavity and into the opening, and released to at least partially revert back to the free shape such that the stem portion fills the opening and the head portion abuts an inner surface of the skull as well as dura, thereby securing the closure device in position and sealing the opening.

II. The bioresorbable closure device as set forth I. wherein the head portion is foldable along a longitudinal axis in a distal direction.

III. The closure device as set forth in any one of claims I. or II. further comprising at least one active agent.

IV. The closure device as set forth in any one of I. through III. wherein the stem portion and or the head portion has a cylindrical shape.

V. The closure device as set forth in any one of I. through IV. wherein the stem portion is cylindrical and the head portion is concentrically disposed on the distal end of the stem portion and disc shaped.

VI. The closure device as set forth in any one of I. through V. wherein the stem portion and/or the head portion has a rectangular cross-sectional profile.

VII. The closure device as set forth in any one of I. through VI. wherein the film layer comprises polysiloxane.

VIII. The closure device as set forth in any one of I. through VII. wherein the film layer comprises polyurethane.

IX. The closure device as set forth in VII. wherein the film layer and the foam base are bonded to one another via hydrogen bonding and substantially free of covalent bonds therebetween.

X. The closure device as set forth in any one of I. through IX. wherein removal of the film layer from the foam base results in cohesive failure of the foam base at a bond interface therebetween.

XI. The closure device as set forth in any one of I. through X. wherein a bond interface between the film layer and the foam base is free of adhesive.

XII. The closure device as set forth in any one of I. through IX. wherein the phase-separated polymer is independently selected from the group consisting of polyesters, polyethers, polyhydroxyacids, polylactones, polyetheresters, polycarbonates, polydioxanes, polyanhydrides, polyurethanes, polyester(ether)urethanes, polyurethane urea, polyamides, polyesteramides, poly-orthoesters, polyaminoacids, polyphosphonates, polyphosphazenes, and combinations thereof.

XIII. The closure device as set forth in any one of I. through XII. wherein the phase-separated polymer is a polyurethane foam including amorphous segments and crystalline segments, the crystalline segments formed via hydrogen bonding.

XIV. The closure device as set forth in XIII wherein the crystalline segments in the polyurethane foam comprise a reaction product of 1,4 butanediol and 1,4 diisocyanatobutane.

XV. The closure device as set forth in XIII or XIV. wherein the amorphous segments in the polyurethane foam comprise a polyalkylene glycol.

XVI. The closure device as set forth in XV. wherein molecules within the polyurethane foam are arranged so that that the crystalline segments and the amorphous segments stack in an alternating configuration to provide a 3-dimensional porous structure which is strengthened via hydrogen bonding between the stacked crystalline segments.

One or more of the values described above may vary by ±5%, ±10%, ±15%, ±20%, ±25%, etc., so long as the variance remains within the scope of the disclosure. Each member may be relied upon individually and or in combination and provides adequate support for specific examples within the scope of the appended claims. The subject matter of all combinations of independent and dependent claims, both singly and multiply dependent, is herein expressly contemplated. The disclosure is illustrative, including words of description rather than of limitation. Many modifications and variations of the present disclosure are possible in light of the above teachings, and the disclosure may be practiced otherwise than as specifically described herein.

All combinations of the aforementioned examples throughout the entire disclosure are hereby expressly contemplated in one or more non-limiting examples even if such a disclosure is not described verbatim in a single paragraph or section above. In other words, an expressly contemplated example may include any one or more elements described above selected and combined from any portion of the disclosure.

It is also to be understood that any ranges and subranges relied upon in describing various examples of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various examples of the present disclosure, and such ranges and subranges may be further delineated into relevant halves, thirds, quarters, fifths, and so on. As just one example, a range "of from 0.1 to 0.9" may be further delineated into a lower third, i.e. from 0.1 to 0.3, a middle third, i.e. from 0.4 to 0.6, and an upper third, i.e. from 0.7 to 0.9, which individually and collectively are within the scope of the appended claims, and may be relied upon individually and/or collectively and provide adequate support for specific examples within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific examples within the scope of the appended claims. Finally, an individual number within a disclosed range may be relied upon and provides adequate support for specific examples within the scope of the appended claims. For example, a range "of from 1 to 9" includes various individual integers, such as 3, as well as individual numbers including a decimal point (or fraction), such as 4.1, which may be relied upon and provide adequate support for specific examples within the scope of the appended claims.

Several examples have been discussed in the foregoing description. However, the examples discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A system for trans-nasally closing an opening in a base of a skull, the system including:
   a bioresorbable foam closure device for trans-nasally closing an opening in a base of a skull, the device comprising a stem portion having a proximal end and a distal end, and a head portion at the distal end having at least one dimension being larger than the stem portion, the stem portion comprising a first phase-separated polymer having amorphous segments and crystalline segments, and the head portion comprising a second phase-separated polymer having amorphous segments and crystalline segments, the first phase-separated polymer and the second phase-separated polymer being the same or different, wherein the stem portion is formed from a phase-separated polymer and has a porosity of greater than 80%; and
   a surgical tool comprising:
      a body defining an inner channel, the body having a handle, a dispensing tip, and a central section therebetween, the dispensing tip having a tapered profile between a first region and a second region, the first region having a greater diameter than the second region; and
      a shaft moveably disposed in the inner channel of the body, the shaft having a control surface at a proximal region and a deformable head at a distal region, the shaft and the deformable head cooperate to define a lumen to accommodate a portion of the closure device.

2. The system as set forth in claim 1, wherein the head portion is collapsible along a longitudinal axis in a distal direction.

3. The system as set forth in claim 1, wherein the first and/or second phase-separated polymer is a polyurethane foam including the amorphous segments and the crystalline segments, wherein the crystalline segments are formed via hydrogen bonding.

4. The system as set forth in claim 1, wherein the bioresorbable foam closure device further comprises at least one active agent.

5. The system as set forth in claim 1, wherein the head and the stem portions share a longitudinal axis and a radius of the head portion relative to the longitudinal axis is greater than a radius of the stem portion relative to the longitudinal axis.

6. The system as set forth in claim 1, wherein the head portion comprises a film layer and a foam base.

7. The system as set forth in claim 6, wherein:
   a porosity of the film layer is less than a porosity of the foam base; and/or
   the film layer is disposed at the distal end of the closure device and the foam base of the head is disposed between the film layer and the stem portion.

8. The system as set forth in claim 1, wherein:
   the stem portion and/or the head portion has a cylindrical shape; and/or
   the head portion has a greater perimeter and/or diameter than the stem portion.

9. The system as set forth in claim 1, wherein the dispensing tip includes sidewalls that define the tapered profile, and wherein upon actuation of the control surface, the shaft is moveable within the inner channel to move the deformable head proximally such that the sidewalls of the dispensing tip engage and deform the deformable head to load the closure device into the surgical tool.

10. The system as set forth in claim 1, wherein the control surface comprises:
   a thumb stirrup; and/or
   a pair of finger saddles, such that a user may insert their thumb into the thumb stirrup and loop their index and middle fingers over the finger saddles and actuate the surgical tool with one hand.

11. The system as set forth in claim 1, wherein a distal end of the body includes a flared portion having a diameter, which increases along a longitudinal axis in a radial direction.

12. The system as set forth in claim 1, wherein a distal end of the body includes an alignment flange, wherein the alignment flange rests on an outer surface of the skull when the dispensing tip is inserted into the opening such that the closure device is positioned in the opening and does not penetrate too far into a cranial cavity.

13. The system as set forth in claim 1, wherein the central section of the body comprises a malleable material and the shaft comprises a flexible material such that a shape of the surgical tool may be changed to facilitate use of the surgical tool in a nasal cavity.

14. The system as set forth in claim 1, wherein the body has an inner surface which defines the inner channel and also a stop surface, wherein a stop shelf extends radially around the shaft and cooperates with the stop surface to stop movement of the shaft along a longitudinal axis in a distal direction.

15. A method of trans-nasally closing an opening in a base of a cranium having an inner surface and defining a cranial cavity with a surgical tool and a bioresorbable foam closure device, said method comprising the steps of:
   providing the closure device having a stem portion having a proximal end and a distal end, and a head portion at the distal end having at least one dimension being larger than the stem portion, the stem portion comprising a first phase-separated polymer having amorphous segments and crystalline segments, and the head portion comprising a second phase-separated polymer having amorphous segments and crystalline segments, the first phase-separated polymer and the second phase-separated polymer being the same or different, wherein the stem portion is formed from a phase-separated polymer and has a porosity of greater than 80%;
   deforming at least the head portion of the closure device from a free shape to a deformed shape;
   inserting the deformed head portion of the closure device through a nasal cavity and through the opening such that the head portion is in the cranial cavity and the stem portion extends through the opening and into the nasal cavity; and
   releasing the closure device such that the closure device at least partially reverts to the free shape such that the stem portion fills the opening and the head portion abuts an inner surface of the cranium as well as dura, thereby securing the closure device in position and sealing the opening.

16. The method as set forth in claim 15, further comprising the step of providing a surgical tool for closing the opening in a skull with the closure device.

17. The method as set forth in claim 16, further comprising the step of loading the closure device into the surgical tool, and wherein the step of deforming is further defined as moving the deformable head proximally such that a dispensing tip on the surgical tool engages the stem portion of the closure device and deforms the deformable head to load the closure device into the surgical tool.

18. The method as set forth in claim 17, further comprising the step of actuating a shaft on the surgical tool from a disengaged position to an engaged position to deform the closure device from the free shape to the deformed shape and load the closure device within the dispensing tip.

19. The method as set forth in claim 18, further comprising the step of actuating the shaft from the engaged position to the disengaged position to release the closure device in the opening.

20. The method as set forth in claim 17, wherein the closure device is compressed during the step of deforming and expands during the step of releasing.

* * * * *